(12) United States Patent
Yang et al.

(10) Patent No.: US 11,773,431 B2
(45) Date of Patent: Oct. 3, 2023

(54) DIAGNOSTIC KIT, DIAGNOSTIC METHOD, AND DIAGNOSTIC APPARATUS

(71) Applicant: GWANGJU INSTITUTE OF SCIENCE AND TECHNOLOGY, Gwangju (KR)

(72) Inventors: Sung Yang, Gwangju (KR); Sung A Hong, Gwangju (KR)

(73) Assignee: Gwangju Institute of Science and Technology, Gwangju (KR)

(*) Notice: Subject to any disclaimer, the term of this patent is extended or adjusted under 35 U.S.C. 154(b) by 935 days.

(21) Appl. No.: 16/629,926

(22) PCT Filed: Jul. 10, 2018

(86) PCT No.: PCT/KR2018/007818
§ 371 (c)(1),
(2) Date: Jan. 9, 2020

(87) PCT Pub. No.: WO2019/013530
PCT Pub. Date: Jan. 17, 2019

(65) Prior Publication Data
US 2021/0139961 A1    May 13, 2021

(30) Foreign Application Priority Data
Jul. 11, 2017  (KR) .................. 10-2017-0087763

(51) Int. Cl.
*C12Q 1/6825*  (2018.01)
*G01N 27/327*  (2006.01)

(52) U.S. Cl.
CPC ....... *C12Q 1/6825* (2013.01); *G01N 27/3276* (2013.01)

(58) Field of Classification Search
CPC ....... B01L 3/00; C12Q 1/6825; C12Q 1/6886; C12Q 2522/101; C12Q 2527/146;
(Continued)

(56) References Cited

U.S. PATENT DOCUMENTS

2008/0254455 A1  10/2008  Wang et al.
2013/0346975 A1  12/2013  Okano
2015/0219594 A1   8/2015  Vulto et al.

FOREIGN PATENT DOCUMENTS

JP    2009022268 A    2/2009
KR    101523174 B1    5/2015
(Continued)

OTHER PUBLICATIONS

Yin et al., Biosensors and Bioelectronics, 51, 2014 103-108 (Year: 2014).*
(Continued)

*Primary Examiner* — Gurpreet Kaur
(74) *Attorney, Agent, or Firm* — Heidi Eisenhut; LOZA & LOZA, LLP

(57) ABSTRACT

A diagnosis kit is disclosed. The diagnosis kit according to an embodiment of the present invention includes a concentration channel into which a sample containing a methylated DNA is introduced, a concentration chamber connected to the concentration channel, wherein the methylated DNA is concentrated by an ion concentration polarization (ICP) phenomenon and moves to the concentration chamber, a sensing chamber connected to the concentration chamber to allow the methylated DNA inside the concentration chamber to move, allow the methylated DNA moved from inside of the concentration chamber to be hybridized, and allow a (Continued)

methylated DNA binding protein to be bound to the hybridized methylated DNA, and a sensor configured to acquire a first electrochemical signal inside the sensing chamber when the methylated DNA is hybridized and acquire a second electrochemical signal inside the sensing chamber when the methylated DNA binding protein is bound.

14 Claims, 13 Drawing Sheets

(58) Field of Classification Search
CPC ........ C12Q 2537/164; C12Q 2600/154; G01N 27/3275; G01N 27/3276; G01N 33/53; G01N 33/574
See application file for complete search history.

(56) References Cited

FOREIGN PATENT DOCUMENTS

| KR | 1020160081379 | A | 7/2016 |
| KR | 101754845 | B1 | 7/2017 |
| WO | 2016049698 | A1 | 4/2016 |

OTHER PUBLICATIONS

Kim et al., Nature, Scientific Reports, 2017, 1-12 (Year: 2017).*
PCT/KR2018/007818. International Search Report & Written Opinion (dated Feb. 22, 2019). 12 pages.
Kurita, Ryoji et al., "Microfluidic platforms for DNA methylation analysis", Lab on a Chip, 2016, 16, pp. 3631-3644, published Aug. 2, 2016, Royal Society of Chemisty. 14 pages.
Son, Seok Young et al., "Engineered Nanofluidic Preconcentration Devices by Ion Concentration Polarization", BioChip J. (2016), 10(4), pp. 251-261, published Apr. 29, 2016, The Korean BioChip Society and Springer. 11 pages.
Almeida, Mafalda et al., "Epigenetic regulation of EFEMP1 in prostate cancer: biological relevance and clinical potential", Journal of Cellular and Molecular Medicine, vol. 18, No. 11, pp. 2287-2297, Received: Apr. 3, 2014; Accepted: Jul. 18, 2014, John Wiley & Sons Ltd and Foundation for Cellular and Molecular Medicine. 11 pages.
Gonzalgo, Mark L. et al., "Prostate Cancer Detection by GSTP1 Methylation Analysis of Postbiopsy Urine Specimens", Clinical Cancer Research, vol. 9, pp. 2673-2677, Jul. 2003, American Association for Cancer Research. 6 pages.

* cited by examiner

-SH ssDNA
Methylated cNDA
Meraptohexanol
Silica nanoparticle (SiNP)
Methyl binding domain protein (MBD 1)

(a)  (b)

- -SH ssDNA
- Methylated cNDA
- Meraptohexanol
- Silica nanoparticle (SiNP)
- Methyl binding domain protein (MBD 1)

(a)

(b)

(a)

(b)

(a)

(b)

(a)

(b)

DIAGNOSTIC KIT, DIAGNOSTIC METHOD, AND DIAGNOSTIC APPARATUS

TECHNICAL FIELD

The present invention relates to a diagnosis kit that is capable of calculating a concentration of a methylation DNA and a level of methylation, a diagnosis method, and a diagnosis device.

BACKGROUND ART

Prostate cancer is a malignant tumor that occurs in the prostate and most commonly occurs in men in developed countries and also is a leading cause of death from the cancer.

Aberrant DNA methylation is a common feature of the human cancers including the prostate cancer. Therefore, studies for diagnosing the cancer using these characteristics have been actively conducted.

A dual pyrosequencing method is a method capable of measuring the DNA methylation very quantitatively, but has a limitation that it is time consuming and complex, and requires large and expensive equipment and skilled practitioners.

DNA methylation electrochemical biosensors have advantages of lower detection limits by using a labeled method. However, separate electrochemical labelers are required, and there are limitations that studies of complex detection on a concentration of a methylation gene and a level of methylation associated with cancer diagnosis and studies on clinically significant samples such as blood or urine have not been conducted.

DISCLOSURE OF THE INVENTION

Technical Problem

The present invention is to solve the above problems, and an object of the present invention is to provide a diagnosis kit that is capable of calculating a concentration of a methylated DNA and a level of methylation, a diagnosis method, and a diagnosis device.

Technical Solution

A diagnosis kit according to an embodiment of the present invention includes a concentration channel into which a sample containing a methylated DNA is introduced, a concentration chamber connected to the concentration channel, wherein the methylated DNA is concentrated by an ion concentration polarization (ICP) phenomenon and moves to the concentration chamber, a sensing chamber connected to the concentration chamber to allow the methylated DNA inside the concentration chamber to move, allow the methylated DNA moved from inside of the concentration chamber to be hybridized, and allow a methylated DNA binding protein to be bound to the hybridized methylated DNA, and a sensor configured to acquire a first electrochemical signal inside the sensing chamber when the methylated DNA is hybridized and acquire a second electrochemical signal inside the sensing chamber when the methylated DNA binding protein is bound.

In this case, the diagnosis kit may further includes a first valve configured to allow the concentration chamber and the sensing chamber to communicate with each other or block the communication between the concentration chamber and the sensing chamber and a second valve configured to allow the concentration channel and the concentration chamber to communicate with each other or block the communication between the concentration channel and the concentration chamber, wherein the second valve may be configured to allow the concentration channel and the concentration chamber to communicate with each other while the methylated DNA is concentrated and block the communication between the concentration channel and the concentration chamber when the methylated DNA moves into the concentration chamber, and the second valve may be configured to allow the concentration chamber and the sensing chamber to communicate with each other after blocking the communication between the concentration channel and the concentration chamber.

In this case, the diagnosis kit may further include a third valve configured to press the inside of the concentration chamber when the first valve allows the concentration chamber and the sensing chamber to communicate with each other.

In this case, the first valve may be configured to block the communication between the concentration chamber and the sensing chamber when the concentration chamber and the sensing chamber communicate with each other so that the methylated DNA within the concentration chamber moves to the sensing chamber.

The diagnosis kit may further include a fourth valve configured to block the communication between the sensing chamber and the outside in addition to the blocking of the communication between the concentration chamber and the sensing chamber through the first valve.

The first electrochemical signal may be a current value used to calculate a concentration of the methylated DNA, and the second electrochemical signal may be a current value used to calculate a level of methylation of the methylated DNA in addition to the concentration of the methylated DNA.

The diagnosis kit may be a diagnosis kit for diagnosing prostate cancer, and the hybridization may be a process of binding ssDNA having a sequence complementary to GSTP1 or EFEMP1 to the methylated DNA.

A diagnosis method according to an embodiment of the present invention includes concentrating a methylated DNA by an ion concentration polarization (ICP) phenomenon to move to a concentration chamber, allowing the methylated DNA within the concentration chamber to move to a sensing chamber, acquiring a first electrochemical signal within the sensing chamber when the methylated DNA moving to the sensing chamber is hybridized;

binding a methylated DNA binding protein to the hybridized DNA, and acquiring a second electrochemical signal within the sensing chamber when the methylated DNA binding protein is bound.

In this case, the diagnosis method may further include allowing a concentration chamber channel and the concentration chamber to communicate with each other while the methylated DNA is concentrated, blocking the communication between the concentration chamber channel and the concentration chamber when the methylated DNA moves to the concentration chamber; and allowing the concentration chamber and the sensing chamber to communicate with each other after blocking the communication between the concentration chamber channel and the concentration chamber.

In this case, the moving of the methylated DNA within the concentration chamber to the sensing chamber may include pressing the inside of the concentration chamber when the concentration chamber and the sensing chamber communicate with each other.

In this case, the diagnosis method may further include blocking the communication between the concentration chamber and the sensing chamber when the concentration chamber and the sensing chamber communicate with each other so that the methylated DNA within the concentration chamber moves to the sensing chamber.

In this case, the blocking of the communication between the concentration chamber and the sensing chamber may include blocking communication between the sensing chamber and the outside in addition to the blocking of the communication between the concentration chamber and the sensing chamber through a first valve.

The first electrochemical signal may be a current value used to calculate a concentration of the methylated DNA, and the second electrochemical signal may be a current value used to calculate a level of methylation of the methylated DNA in addition to the concentration of the methylated DNA.

The diagnosis method may be performed by a diagnosis kit for diagnosing prostate cancer, and the hybridization may be a process of binding ssDNA having a sequence complementary in complementary in GSTP1 or EFEMP1.

A diagnosis device according to an embodiment of the present invention includes a diagnosis kit and a controller, wherein the diagnosis kit includes a concentration channel into which a sample containing a methylated DNA is introduced, a concentration chamber connected to the concentration channel and condensed with the methylated DNA by an ion concentration polarization (ICP) phenomenon, a sensing chamber connected to the concentration chamber to allow the methylated DNA inside the concentration chamber to move, allow the methylated DNA moving to the concentration chamber to be hybridized, and allow a methylated DNA binding protein to be bound to the DNA; and a sensor configured to acquire a first electrochemical signal inside the sensing chamber when the methylated DNA is hybridized and acquire a second electrochemical signal inside the sensing chamber when the methylated DNA binding protein is bound, wherein the controller may calculate a concentration of the methylated DNA and a degree of methylation of the methylated DNA based on the first electrochemical signal and the second electrochemical signal.

In this case, the diagnosis device may further include a first valve configured to allow the concentration chamber and the sensing chamber to communicate with each other or block the communication between the concentration chamber and the sensing chamber, a second valve configured to allow the concentration channel and the concentration chamber to communicate with each other or block the communication between the concentration channel and the concentration chamber, a third valve configured to press the inside of the concentration chamber, and a fourth valve configured to block communication between the sensing chamber and the outside, wherein the controller is configured to control the second valve so as to allow the concentration channel and the concentration chamber to communicate with each other while the methylated DNA is concentrated and block the communication between the concentration channel and the concentration chamber when the methylated DNA moves into the concentration chamber, control the first valve so as to allow the concentration chamber and the concentration and the sensing chamber to communicate with each other after blocking the communication between the concentration channel and the concentration chamber, control the third valve so as to press the inside of the concentration chamber when the concentration chamber and the sensing chamber communicate with each other through the first valve, and control the first valve so as to block the communication between the concentration chamber and the sensing chamber and control the fourth valve so as to block the communication between the sensing chamber and the outside when the methylated DNA within the concentration chamber moves to the sensing chamber.

Advantageous Effects

According to the present invention, since the concentration chamber and the sensing chamber are provided in one kit, and the valve is disposed in the one kit, the concentration, the movement, the incubation, the electrochemical sensing may be all possible in the one kit, and thus, there may be advantages to detect the concentration of the DNA and the level of the methylation at a time.

In addition, the diagnosis kit according to the present invention may use the microfluidic chip to detect the level of the DNA methylation with the small amount of sample (10 μL).

In addition, the methylated DNA that is the target may be detected with the relatively short time (within 2 hours after putting the sample) in the label-free manner without the separate marker.

In addition, the detection limit may be improved through the sample concentration, and since the urine sample of the human is directly used and diagnosed, the convenience may be improved.

In addition, the prostate cancer gene desired to be detected may be spiked to the urine sample of the human and thus detected.

MODE FOR CARRYING OUT THE INVENTION

Hereinafter, embodiments disclosed in this specification is described with reference to the accompanying drawings, and the same or corresponding components are given with the same drawing number regardless of reference number, and their duplicated description will be omitted. Furthermore, terms, such as a "module" ad a "unit", are used for convenience of description, and they do not have different meanings or functions in themselves. Moreover, detailed descriptions related to well-known functions or configurations will be ruled out in order not to unnecessarily obscure subject matters of the present disclosure. However, this does not limit the present disclosure within specific embodiments and it should be understood that the present disclosure covers all the modifications, equivalents, and replacements within the idea and technical scope of the present disclosure.

It will be understood that although the ordinal numbers such as first and second are used herein to describe various elements, these elements should not be limited by these numbers. The terms are only used to distinguish one component from other components.

It will also be understood that when an element is referred to as being "'connected to" or "engaged with" another element, it can be directly connected to the other element, or intervening elements may also be present. It will also be understood that when an element is referred to as being 'directly connected to' another element, there is no intervening elements.

The terms of a singular form may include plural forms unless referred to the contrary. In this application, the terms "comprises" or "having" are intended to indicate that there is a feature, number, step, operation, component, part, or combination thereof described in the specification, and one or more other features. It is to be understood that the present invention does not exclude the possibility of the presence or the addition of numbers, steps, operations, components, components, or a combination thereof.

Figure 1:
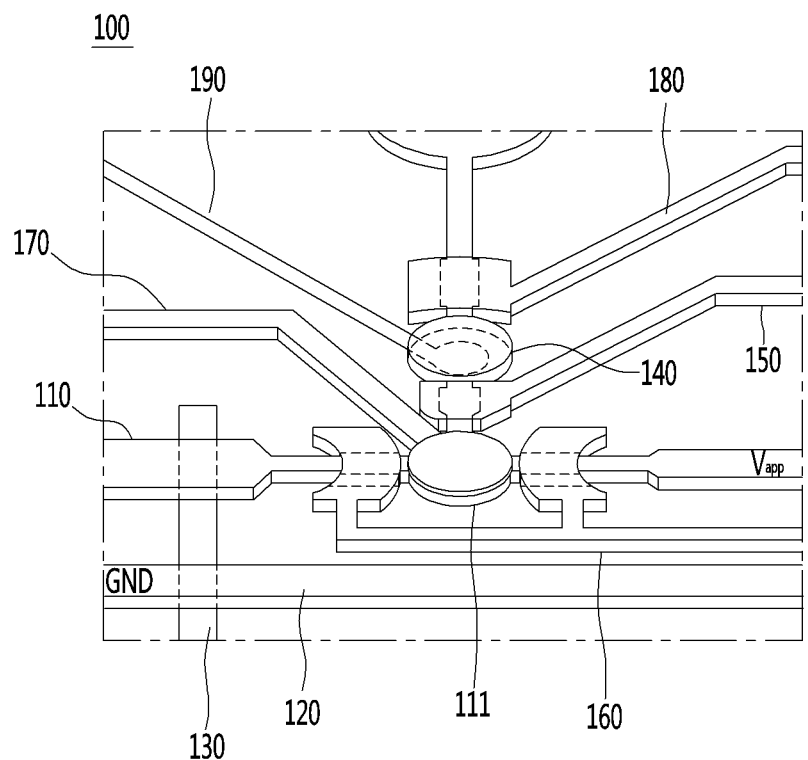
FIG. 1 is a view for explaining a structure of a diagnosis kit according to an embodiment of the present invention.

FIG. 1 is a view for explaining a structure of a diagnosis kit according to an embodiment of the present invention.

A diagnosis kit 100 according to an embodiment of the present invention may include a concentration channel 110, a concentration chamber 111, a buffer 120, a membrane 130, a sensing chamber 140, a first valve 150, a second valve 160, a third valve 170, a fourth valve 180, and at least one of sensors.

A sample may be introduced into the concentration channel 110. In this case, the sample may contain a methylated DNA.

The sample may be a sample containing a DNA of a mammal (preferably, the human). For example, the sample may be a human blood sample, preferably, a urine sample.

Since human urine contains the methylated DNA, the human urine may be used for simple testing without blood extraction or cancer cell biopsy. However, since a small amount of methylated DNA is contained in the human urine, a concentration process is required.

The diagnosis kit 100 may include the patterned membrane 130. Nafion may be used for the membrane.

The concentration channel 110 and the buffer channel 120 may be independently separated from each other within the diagnosis kit 100, and the patterned membrane 130 may be disposed below the concentration channel 110 and the buffer channel 120 to connect the concentration channel 110 to the buffer channel 120.

The concentration chamber 111 may be connected to the concentration channel 110 and may or may not communicate with the concentration channel 110.

The second valve 160 may be disposed between the concentration channel 110 and the concentration chamber 111.

The second valve 160 may allow the concentration channel 110 and the concentration chamber 111 to communicate with each other or may block the communication between the concentration channel 110 and the concentration chamber 111.

Specifically, when the second valve 160 is open, the concentration channel 110 and the concentration chamber 11 may communicate with each other. When the second valve 160 is closed, the communication between the concentration channel 110 and the concentration chamber 111 may be blocked.

The methylated DNA in the sample may be concentrated to move to the concentration chamber 111 by an ion concentration polarization (ICP) phenomenon.

The sensing chamber 140 may be connected to the concentration chamber 111 and may or may not communicate with the concentration chamber 111.

The first valve 150 may be disposed between the concentration channel 110 and the concentration chamber 111.

The first valve 150 may allow the concentration chamber 111 and the sensing chamber 140 to communicate with each other or may block the communication between the concentration chamber 111 and the sensing chamber 140.

In detail, when the first valve 150 is opened, the concentration chamber 111 and the sensing chamber 140 may communicate with each other. When the first valve 150 is closed, the communication between the concentration chamber 111 and the sensing chamber 140 may be blocked.

The methylated DNA that is concentrated to move into the concentration chamber 111 may move to the sensing chamber 140.

In this case, the third valve 170 may press the inside of the concentration chamber 111. In detail, the third valve 170 may be disposed above the concentration chamber 111 to communicate with the inside of the concentration chamber 111. When the first valve 150 is opened so that the concentration chamber 111 and the sensing chamber 140 communicate with each other, air may be introduced into the concentration chamber 111 through the third valve 170. Thus, the methylated DNA within the concentration chamber 111 may move to the sensing chamber 140. Also, while the third valve 170 presses the concentration chamber 111, the fourth valve 180 may be opened to assist the movement of the methylated DNA.

The methylated DNA moving to the sensing chamber 140 may be hybridized within the sensing chamber 140. Also, the methylated DNA binding protein may be bound to the hybridized methylated DNA within the sensing chamber 140.

The fourth valve 180 may be connected to one end of the sensing chamber 140. When the first valve 150 and the fourth valve 180 are closed together, the sensing chamber 140 may be closed.

The sensor may include a sensing electrode 190 disposed on a bottom surface of the sensing chamber 140.

When a first voltage is applied to the sensing electrode 190, the sensor may acquire a first electrochemical signal within the sensing chamber 140. Also, when a second voltage is applied to the sensing electrode 190, the sensor may acquire a second electrochemical signal within the sensing chamber 140.

The sensor may output the first electrochemical signal and the second electrochemical signal. Particularly, the first electrochemical signal and the second electrochemical signal may be current values measured when the voltages are applied to the sensing electrode 190, and the sensor may output the current values.

For example, the sensor may include a display part to display each of the current values. For another example, the sensor may transmit a signal corresponding to the current value to a controller.

The diagnosis kit 100 may be provided as a microfluidic element.

Also, the diagnosis kit 100 may be a diagnosis kit for diagnosing prostate cancer.

The diagnosis kit 100 may be constituted by a plurality of layers. This is illustrated with reference to FIGS. 2 to 3.

Figure 2:
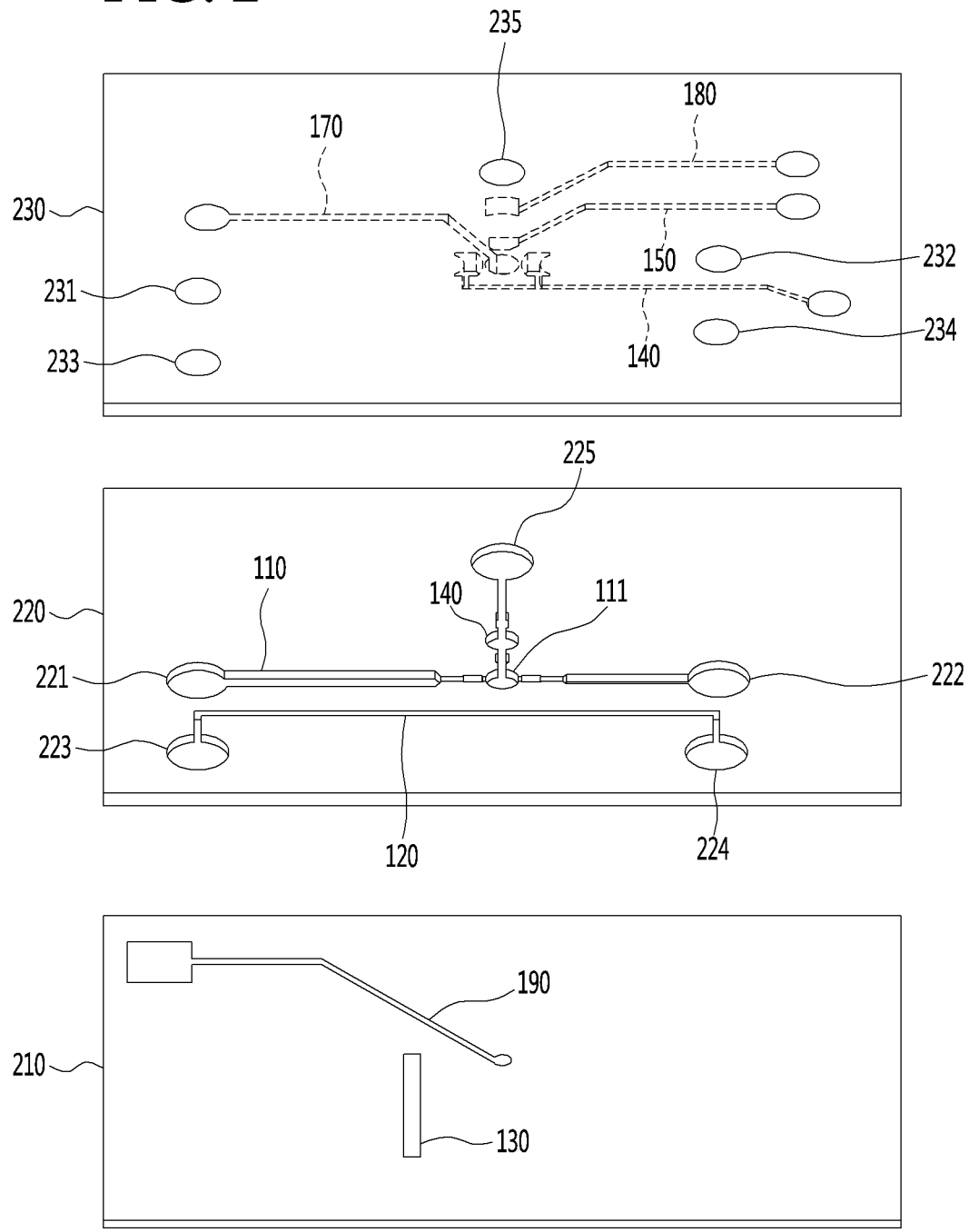
FIG. 2 is a view for explaining the diagnosis kit constituted by a plurality of layers.
Figure 3:
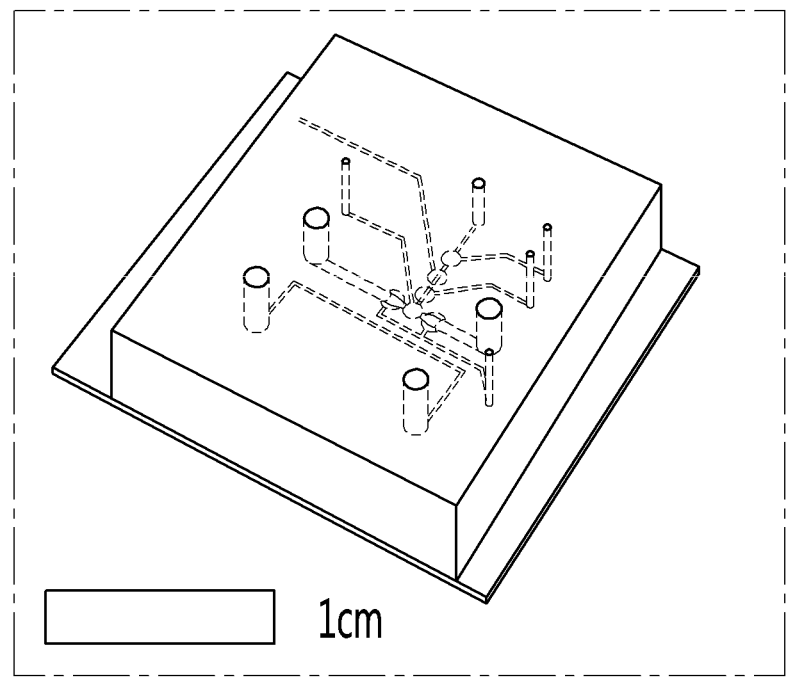
FIG. 3 is a view of the diagnosis kit according to an embodiment of the present invention.

FIG. 2 is a view for explaining the diagnosis kit constituted by the plurality of layers, and FIG. 3 is a view of the diagnosis kit according to an embodiment of the present invention.

The diagnosis kit 100 may include a first layer 210, a second layer 220, and a third layer 230.

The first layer 210 of the plurality of layers may be disposed at the lowermost portion. The patterned Nafion 130 and the sensing electrode 190 may be disposed on a top surface of the first layer 210.

The second layer 220 may be disposed on an upper portion of the first layer 210. The buffer channel 120, the concentration channel 110, the concentration chamber 111, and the sensing chamber 140 may be disposed in the second layer 220.

The third layer 230 may be disposed on an upper portion of the second layer 220. A plurality of valves 150, 160, 170, and 180 may be disposed in the third layer 230.

The plurality of valves 150, 160, 170, and 180 may be patterned on a bottom surface of the third layer 230.

One end of the first valve 150 may be disposed between the concentration chamber 111 and the sensing chamber 140. Also, one end of the second valve 160 may be disposed between the concentration channel 110 and the concentration chamber 111. Also, one end of the third valve 170 may be disposed above the concentration chamber 111, and one end of the fourth valve 180 may be disposed between the sensing chamber 140 and a hole 225 connected to the sensing chamber 140.

The buffer channel 120, the concentration channel 110, the concentration chamber 111, and the sensing chamber 140 disposed in the second layer 220 may vertically communicate with each other. However, since the second layer 220 contacts the lower first layer 210 and the upper third layer, each of the buffer 120, the concentration channel 110, the concentration chamber 111, and the sensing chamber 140 may have closed top and bottom surfaces.

Holes 221 and 222 connected to the concentration channel 110, holes 223 and 224 connected to the buffer channel 120, and a bottom surface of the hole 225 connected to the sensing chamber 140 may contact the first layer 210 so as to be closed. However, the holes 221, 222, 223, 224, and 225 disposed in the second layer 220 may be connected to holes 231, 232, 233, 234, and 235 in the third layer 230, respectively. Accordingly, the holes 221, 222, 223, 224, and 225 in the second layer 220 may communicate with the outside. A sample may be injected into the holes 221, 222, 223, 224, and 225, or the holes 221, 222, 223, 224, and 225 assist movement of the sample.

FIGS. 4 to 9 are views for explaining a diagnosis method using the diagnosis kit according to an embodiment of the present invention.

A diagnosis method using the diagnosis kit will be described with reference to FIG. 1.

A sample containing a methylated DNA may be introduced into a concentration channel 110.

Also, the methylated DNA in the concentration channel 110 may be concentrated by an ion concentration polarization (ICP) phenomenon to move to a concentration chamber 111.

Specifically, a potential may be applied to a right portion Vapp of the concentration channel 110 and a left portion GND of the buffer channel 120. In this case, the right portion Vapp of the concentration channel 110 may be an anode, and the left portion GND of the buffer channel 120 may be a cathode.

Figure 4:
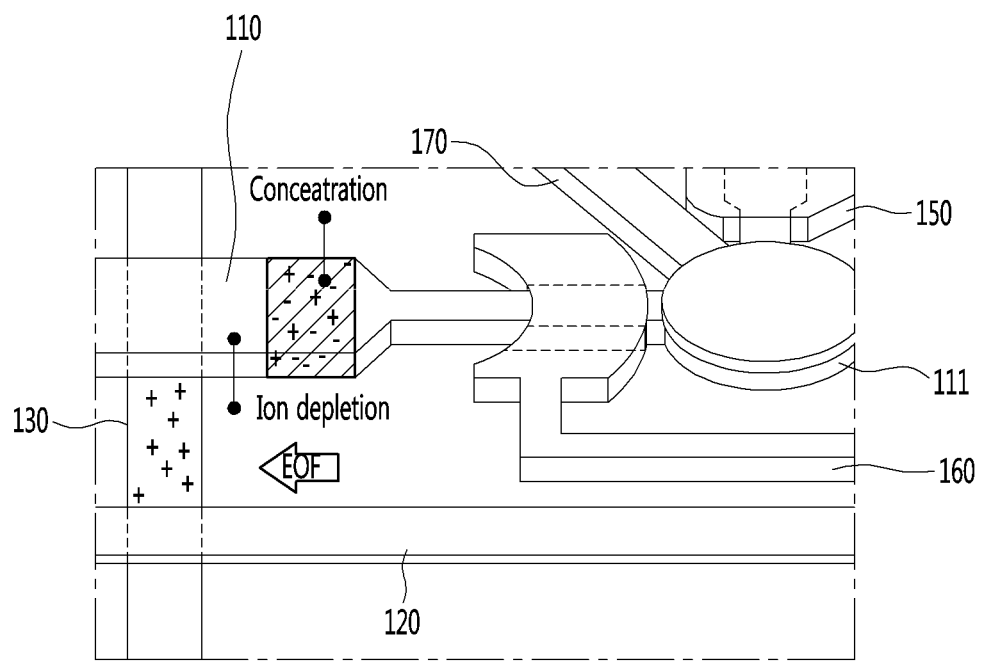
FIGS. 4 to 9 are views for explaining a diagnosis method using the diagnosis kit according to an embodiment of the present invention.

In this case, as illustrated in FIG. 4, positive ions within the concentration channel 110 may move through the Nafion 130 having negative charges, and negative ions may move toward the anode having the positive ions to maintain electrical charge neutrality due to the ion concentration polarization (ICP) phenomenon.

Also, an ion depletion zone (IDZ) in which a strong electric field (E-field) is applied so that no ions exist may be generated, and a DNA having negative charges together with the negative ions may be concentrated on an interface of the ion depletion zone.

Also, as an amount of anion and DNA concentrated at the interface of the ion depletion zone (IDZ) increases, the concentrated methylated DNA may move toward the anode by electrophoretic (EP).

While the methylated DNA is concentrated, the second valve 160 may be maintained in the opened state to allow the concentration channel 110 to communicate with the concentration chamber 111. Also, the first valve 150 may be maintained in the closed state so as to be prevented from being affected on the sensor.

Also, when the concentrated methylated DNA moves toward the anode and then is located in the concentration chamber 111, the second valve may be closed to block the communication between the concentration channel 110 and the concentration chamber 111.

Figure 5:
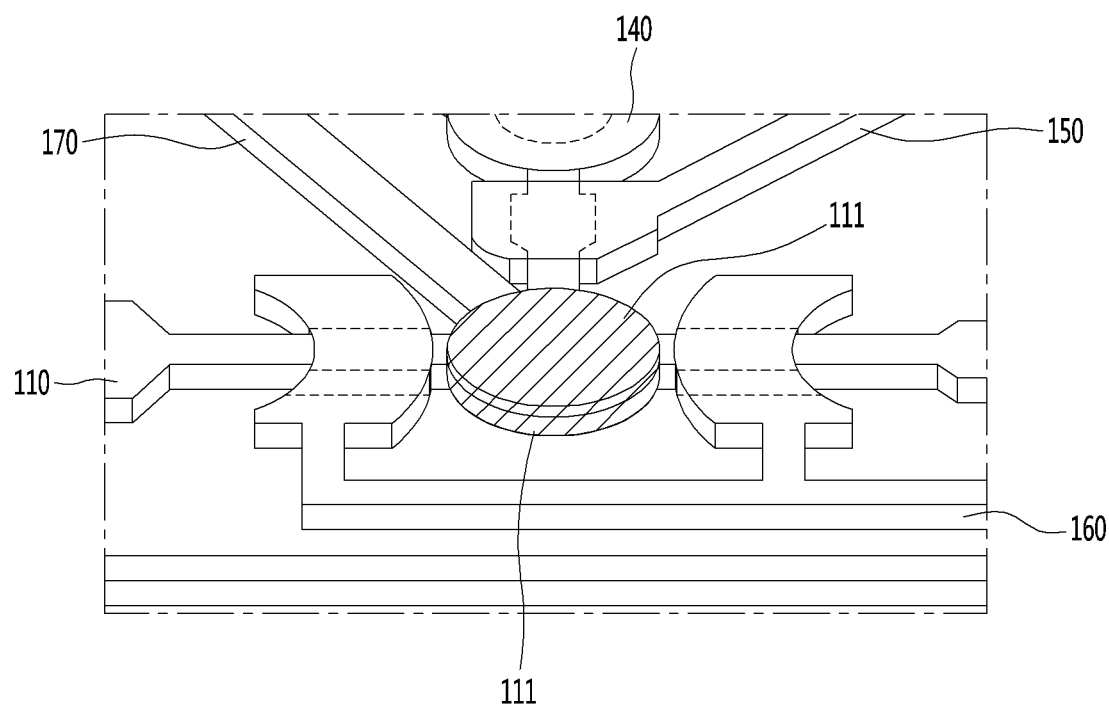

The E-field may be removed in addition to the blocking of the communication between the concentration channel 110 and the concentration chamber 111 to isolate the concentrated methylated DNA. The methylated DNA moving into the concentration chamber 111 is illustrated in FIG. 5.

The methylated DNA in the concentration chamber 110 may move to the sensing chamber 140.

Specifically, as the first valve 150 is opened after blocking the communication between the concentration channel 110 and the concentration chamber 111, the concentration chamber 111 and the sensing chamber 140 may communicate with each other.

In this case, while the concentration chamber 111 and the sensing chamber 140 communicate with each other, the third valve 170 may press the inside of the concentration chamber 111. In this case, the fourth valve 180 may be open, and thus the sensing chamber 140 may communicate with the outside.

Accordingly, when the third valve 170 presses the inside of the concentration chamber 111, the methylated DNA in the concentration chamber 111 may move to the sensing chamber 140.

Figure 6:
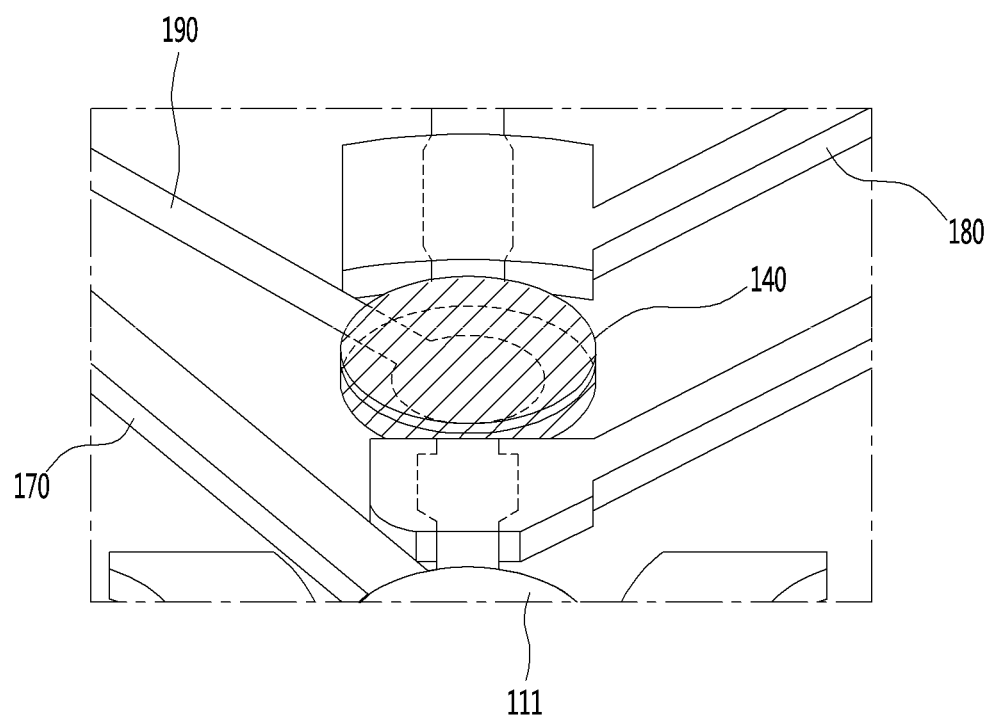
Figure 7:
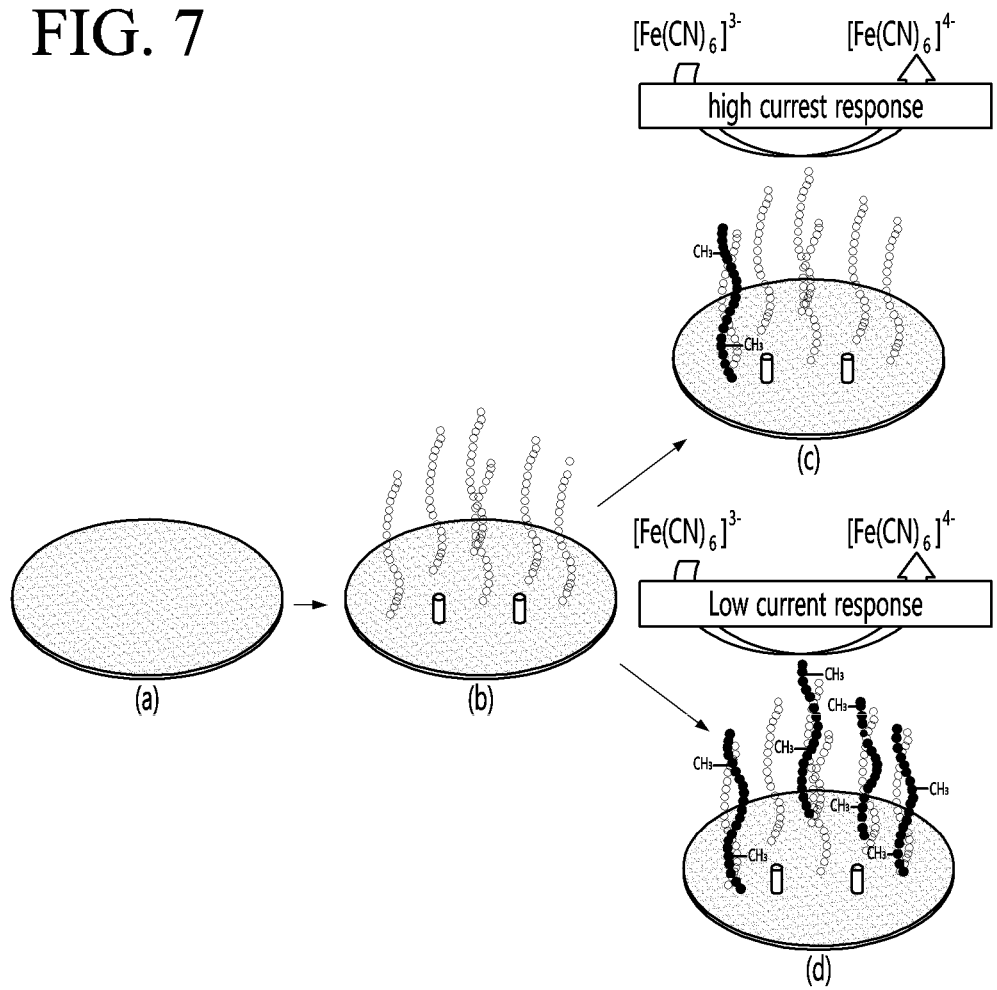
Figure 7:
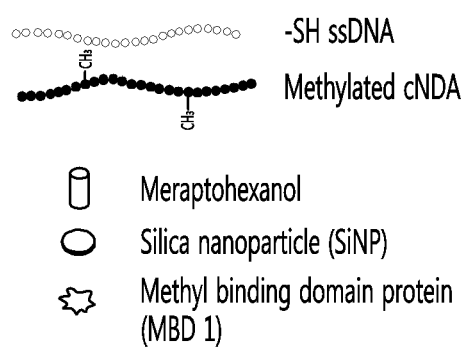
Figure 8:
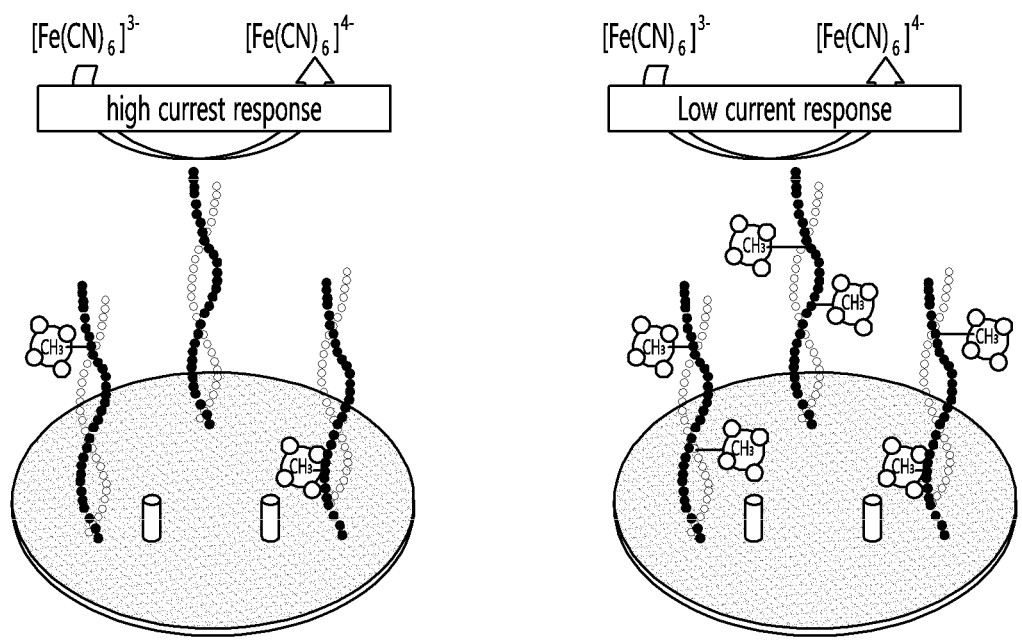
Figure 8:
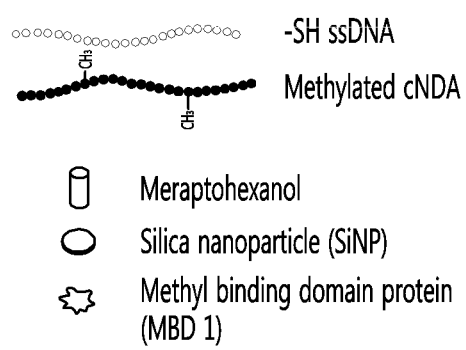
Figure 9:
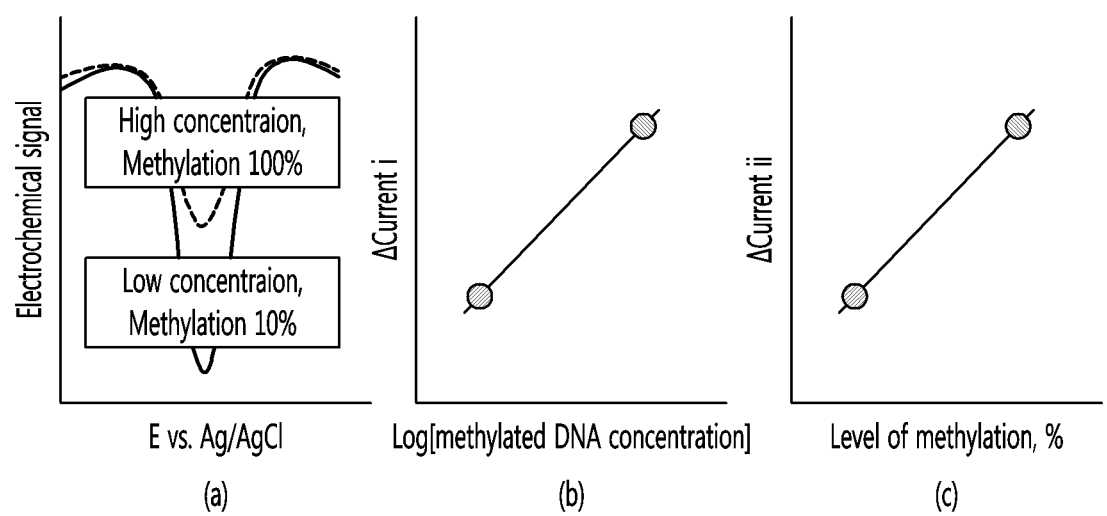

The methylated DNA moving to the sensing chamber 140 is illustrated in FIG. 6.

When the methylated DNA moves to the sensing chamber 140, the first valve 150 and the fourth valve 180 may be closed. Accordingly, the communication between the sensing chamber 140 and the concentration chamber 111 may be blocked, and the communication between the sensing chamber 140 and the outside may be blocked.

The methylated DNA moving to the sensing chamber 140 may be incubated on the sensing electrode 190 disposed on the bottom surface of the sensing chamber 140.

The methylated DNA may be hybridized inside the sensing chamber 140.

Here, the hybridization may be a process of binding ssDNA having a sequence complementary in a target gene to the methylated DNA.

For example, when the diagnosis kit 100 is used for diagnosing the prostate cancer, the ssDNA may be bound to the methylated DNA with the sequence complementary in GSTP1 or EFEMP1.

Referring to the hybridization process in more detail, the electrode surface of the bottom surface of the sensing chamber 140 may be provided as a gold nano surface, and —SH ssDNA may be immobilized on the gold nano surface. In this case, when the methylated DNA moves to the sensing chamber 140, —SH ssDNA may be bound to the methylated DNA having a complementary sequence.

The process of immobilizing the —SH ssDNA is illustrated in FIGS. 7A and 7B, the process of hybridizing the methylated DNA having the low concentration is illustrated in FIG. 7C, and the process of hybridizing the methylated DNA having the high concentration is illustrated in FIG. 7D.

When the methylated DNA is hybridized, the sensor may acquire a first electrochemical signal inside the sensing chamber 140.

Specifically, when methylated DNA is hybridized, and the first voltage is applied to the sensing electrode 190, the sensor may acquire the first electrochemical signal inside the sensing chamber 140.

Here, the first electrochemical signal may be a current value measured when the voltage is applied to the sensing electrode 190.

Since the higher the concentration of the methylated DNA, the more the hybridization (hybridization) occurs, the electron transfer of Fe(CN) 64—/3—may be blocked, and thus the measured current value may decrease. On the other hand, as the concentration of the methylated DNA decreases, the measured current value may increase.

First current Δcurrent i may be calculated by the following equation.

$$\Delta \text{ current } i=-(\text{blank current value}-\text{measured current value})$$

That is, the higher the methylated DNA concentration, the smaller the measured current value. As a result, a difference between the blank current value and the measured current value increases. Therefore, the first current Δcurrent i may increase as the concentration of the methylated DNA is higher. This is illustrated graphically in FIG. 9B.

The first electrochemical signal may be a current value used to calculate the concentration of the methylated DNA.

Specifically, the first current Δcurrent i may be calculated using the first electrochemical signal, and the first current Δcurrent i may be substituted into the equation of the calibration curve and used to calculate the concentration of the methylated DNA. This is described again in FIGS. 13 and 14.

When the first electrochemical signal is acquired, a DNA binding protein may be bound to the hybridized methylated DNA. Here, the DNA binding protein may be methyl binding domain protein (MBD1) that is bound only to methylated sites.

In this case, silica nanoparticles, in which the methyl binding domain protein (MBD1) is conjugated, i.e., MBD1-SiNP may be put into the sensing chamber 140. The MBD1-SiNP may be synthesized based on EDC/NHS conjugation.

The process of binding the MBD1-SiNP to the methylated DNA having a low level of the methylation is illustrated in FIG. 8A, and the process of binding the MBD1-SiNP to the methylated DNA having a high level of the methylation is illustrated in FIG. 8B.

When the methylated DNA binding protein is bound to the methylated DNA, the sensor may acquire a second electrochemical signal inside the sensing chamber 140.

Specifically, when the methylated DNA binding protein is bound to the methylated DNA, and the second voltage is applied to the sensing electrode 190, the sensor may acquire the second electrochemical signal inside the sensing chamber 140.

Here, the second electrochemical signal may be a current value measured when the voltage is applied to the sensing electrode 190.

The higher the level of methylation of methylated DNA, the more the SiNP-MBD1 are bound to block the surface of the electrode. Therefore, the current value measured by blocking the electron transfer of Fe(CN) 64—/3—may decrease. On the other hand, as the level of the methylation of the methylated DNA decreases, the measured current value may increase.

The second current Δcurrent ii may be calculated by the following equation.

$$\Delta\text{current } ii=-(\text{measured current value before binding}-\text{measured current value after binding})$$

The measured current value before the binding may be a current value measured after the hybridization, i.e., a current value corresponding to the first electrochemical signal.

That is, as the level of the methylation of the methylated DNA increases, the measured current value after the binding decreases. As a result, a difference between the measured current value before the binding and the measured current value after the binding may increase. Therefore, the second current Δcurrent ii may increase as the level of the methylation increases. This is illustrated graphically in FIG. 9C.

The second electrochemical signal may be a current value used to calculate the level of the methylation.

Specifically, the second current Δcurrent ii may be substituted into the equation of the calibration curve and used to calculate the level of the methylation of the methylated DNA. This is described again in FIGS. 13 and 14.

Figure 10:
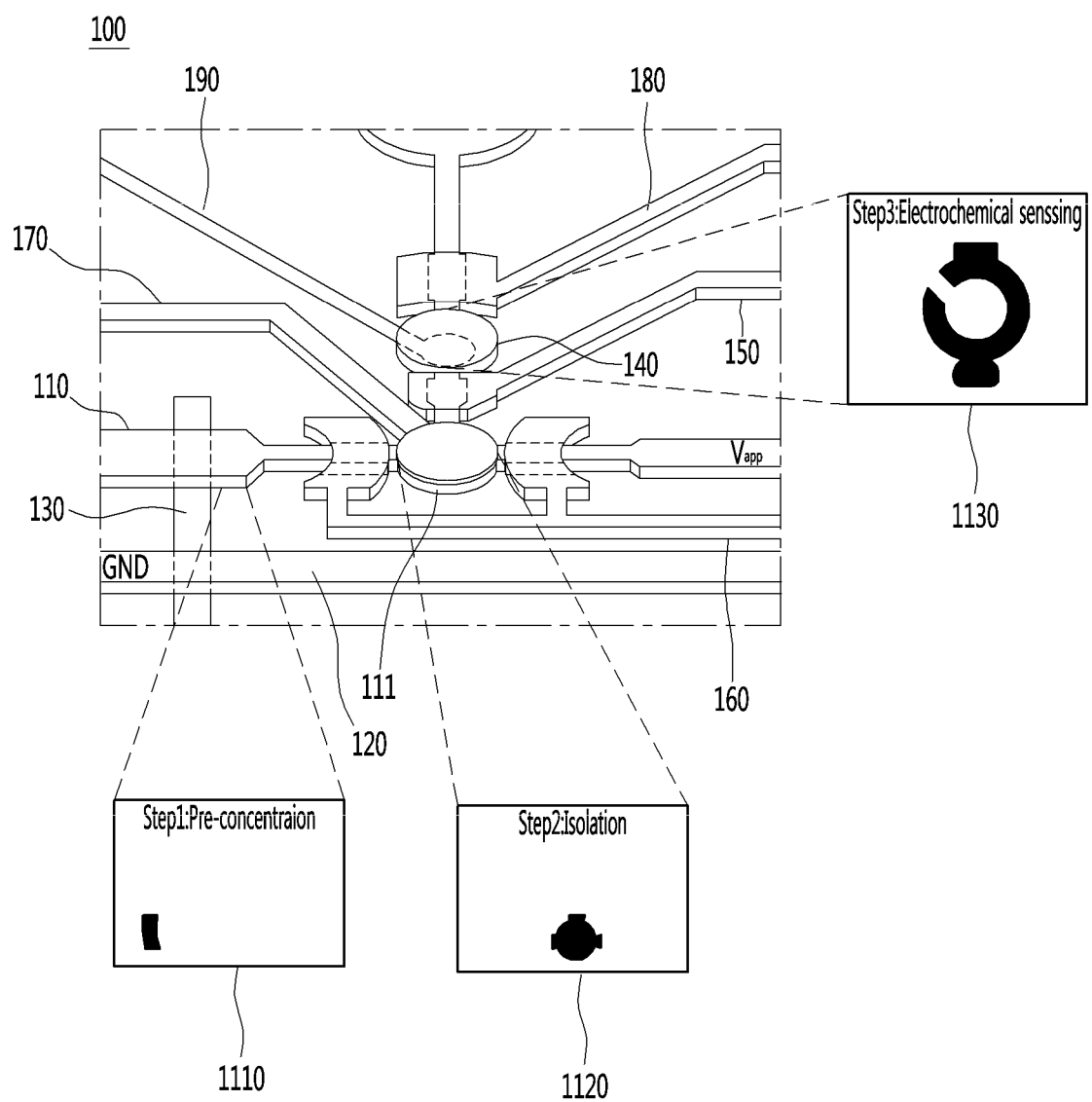
FIG. 10 is a view of a methylated DNA that is concentrated and moves by an ion concentration polarization phenomenon according to an embodiment of the present invention.

FIG. 10 is a view of the methylated DNA that is concentrated and moves by the ion concentration polarization phenomenon according to an embodiment of the present invention.

In order to confirm the concentration phenomenon, a sample containing methylated DNA-cy3 is used.

The first image 1110 illustrates the methylated DNA that is being concentrated in the concentration channel 110, the second image 1120 illustrates the methylated DNA that is isolated in the concentration chamber 111, and the third image 1130 illustrates the methylated DNA moving to the chamber 140.

Figure 11:
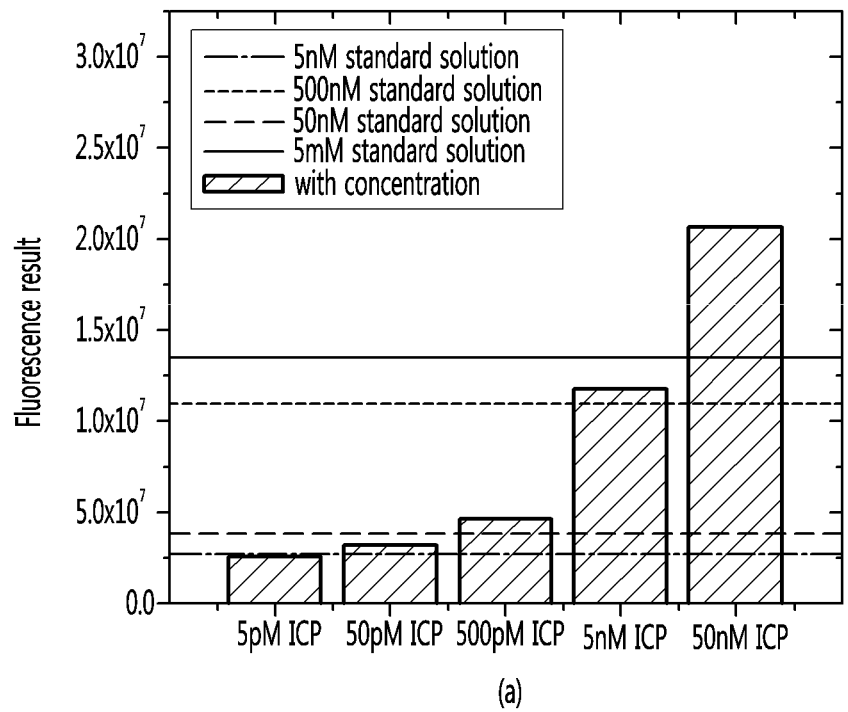
FIG. 11 is a view for explaining a result of concentration using the ion concentration polarization phenomenon.
Figure 11:
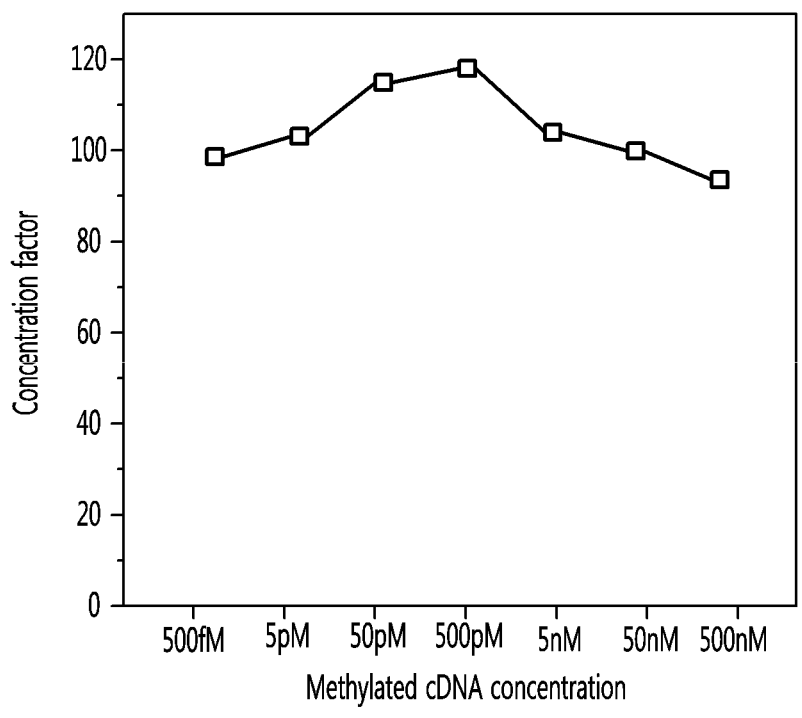

FIG. 11 is a view for explaining a result of concentration using the ion concentration polarization phenomenon.

Brightness for the concentration of the methylated DNA-cy3 was illustrated in FIG. 11A, and a concentration factor for the concentration was illustrated in FIG. 11B.

In order to confirm the phenomenon and degree of the concentration, cy3 were attached to cDNA 5' so as to be observed by fluorescence.

In addition, 500 nM of a methylated DNA-cy3 sample was injected, 100 V/cm E-field was applied, and a fluorescence picture was taken for the process of the concentration for 10 minutes.

In addition, the fluorescence results were compared and analyzed according to the concentration of methylated DNA-cy3 at seven concentrations of 500 fM, 5 pM, 50 pM, 500 pM, 5 nM, 50 nM, and 500 nM.

As a result of calculating a p-value by performing a t-test for each concentration, the p-value was less than 0.0001 at all concentrations. If the p-value is less than 0.0001, it means that two comparison groups are very different, i.e., means that the concentration is good at each concentration.

It was concentrated about 120 times at 50 pM and 500 pM and concentrated about 90 times at 500 nM that is the highest concentration. Thus, it was averagely concentrated about 100 times.

Figure 12:
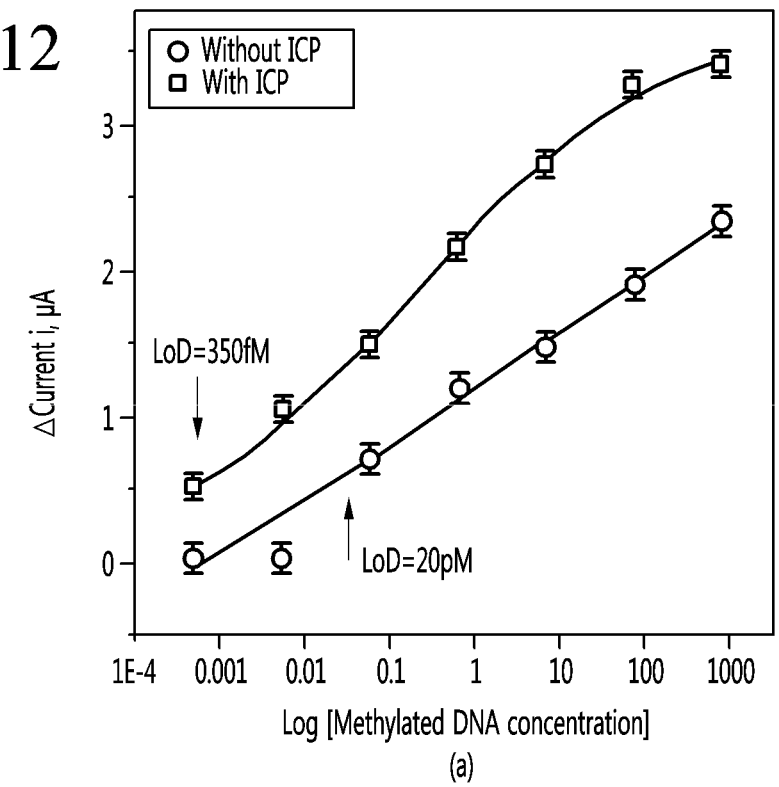
FIG. 12 is a view illustrating a result of electrochemical sensing after any sample is concentrated.
Figure 12:
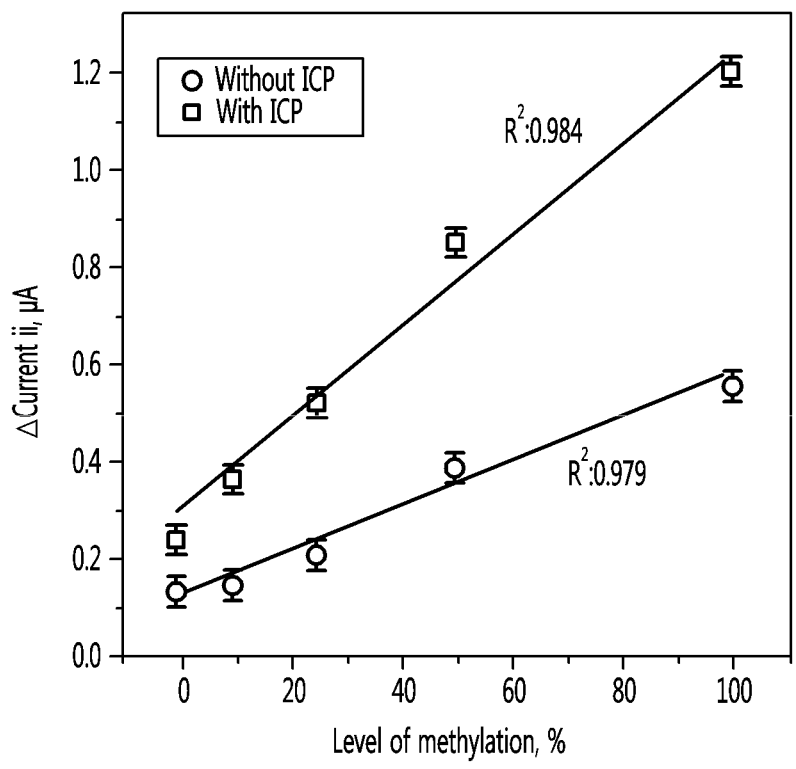

FIG. 12 is a view illustrating a result of the electrochemical sensing after any sample is concentrated.

The electrochemical sensing results of the concentrations according to the concentrations were illustrated in FIG. 12A, and the electrochemical sensing results of the level of the methylation according to the concentrations were illustrated in FIG. 12B.

The electrochemical sensing was performed after preconcentration according to each concentration.

After the concentration for each concentration and also after moving to the sensing chamber 140, the incubation was performed on the electrode for one hour. Thereafter, the DNA that is not hybridized was removed by washing, SiNP-MBD1 was incubated for one hour to measure the current value according to the concentration of the methylated DNA.

When the concentration is not concentrated, the detection limit of 20 pM was shown. On the other hand, when the concentration is performed, the detection limit of 350 fM was shown, resulting in being improved about 57 times. A reason in which the low concentration of the methylated DNA is detected is because 500 fM that is a low concentration is concentrated about 100 times through the ion concentration polarization (ICP), resulting in increasing to a concentration to 50 pM.

Also, when the experiment is performed according to the degree of the methylation at a DNA concentration of 500 pM, the detection limit was 20% when not concentrated, whereas the detection limit was 9% when concentrated.

Figure 13:
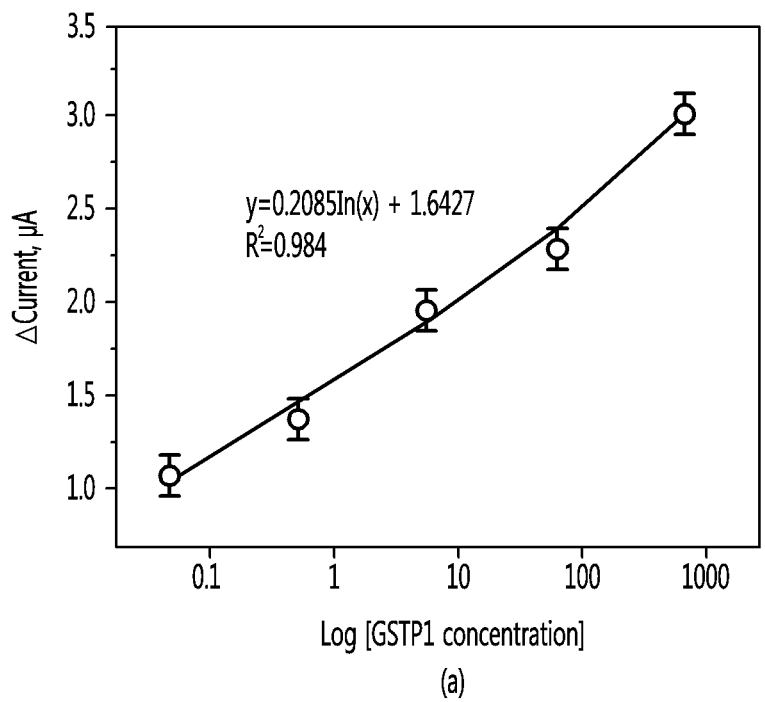
FIGS. 13 to 14 are views illustrating a result of electrochemical sensing using a prostate cancer-related gene.
Figure 13:
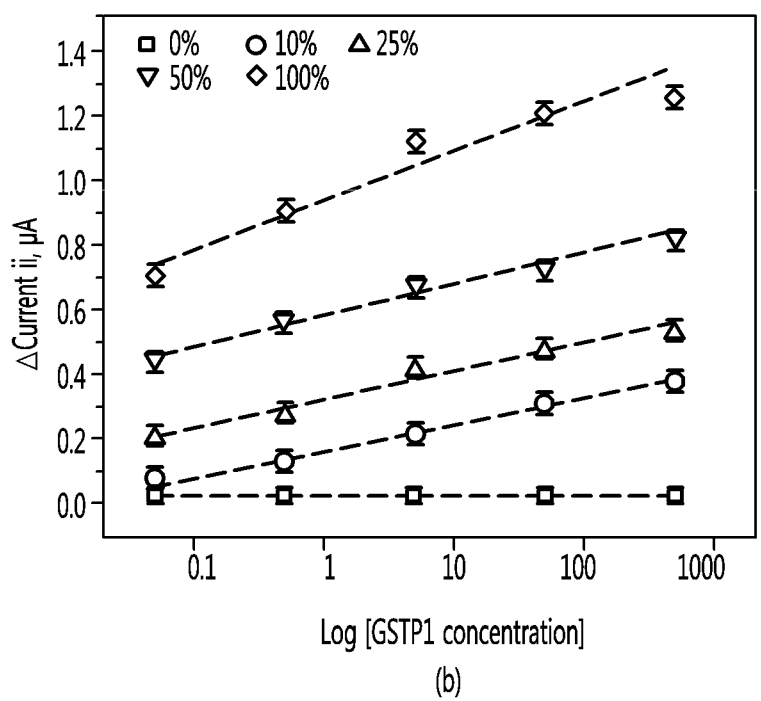
Figure 14:
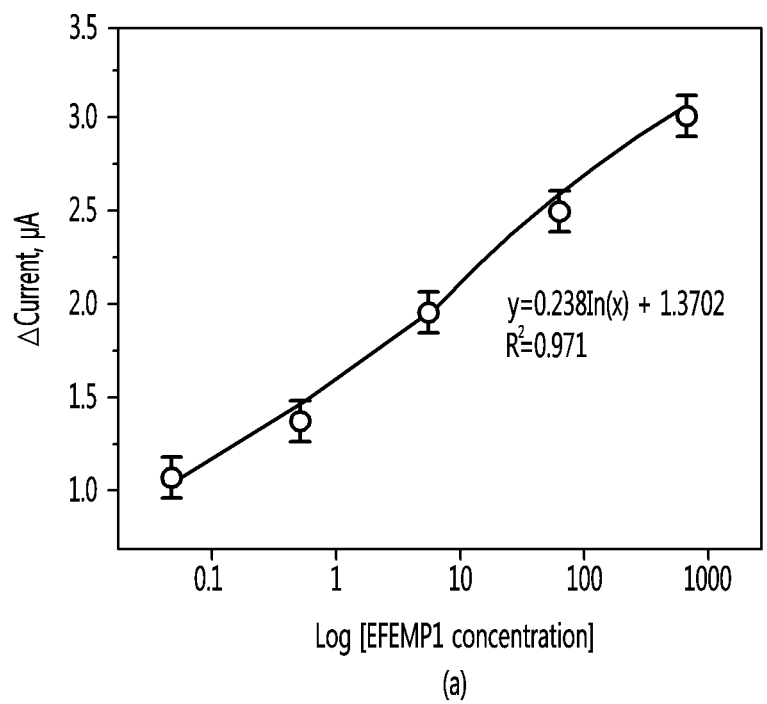
Figure 14:
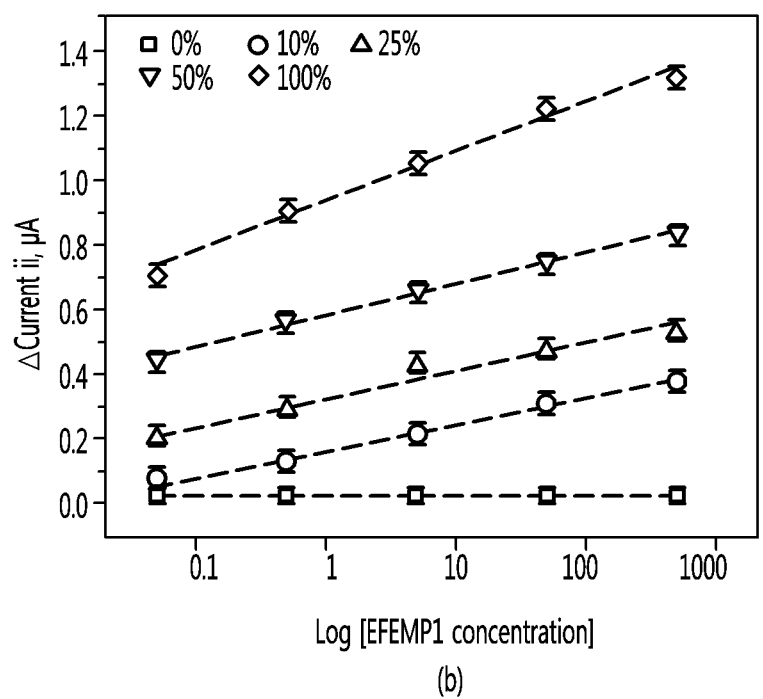

FIGS. 13 to 14 are views illustrating a result of the electrochemical sensing using a prostate cancer-related gene.

The experiment was performed in a manner that detects methylated genes known to be involved in the prostate cancer by using a human urine samples.

Therefore, as illustrated in FIG. 13, the experiment for a first gene (GSTP1) was performed, and as illustrated in FIG. 14, the experiment for a second gene (EFEMP1) was performed.

Among the known sequences, a section containing four CpG islands was selected to synthesize the cy3 at an end of 5', and complementary thiol modified ssDNA was synthesized.

Referring to FIG. 13, the experiment was performed on the concentration and level of the methylation of the methylated DNA from the GSTP1 spiked in the human urine sample.

The concentration ranges of 50 pM, 500 pM, 5 nM, 50 nM, 500 nM, and the level of the methylation ranges of 0%, 10%, 25%, 50%, and 100%.

The concentrated DNA moved to the sensing chamber 140 and then was incubated for 1 hour to acquire the first electrochemical signal.

The measurement results at this time were changed only according to the DNA concentration regardless of the level of the methylation (fixed to 100%). As a result, the methylated DNA from the GSTP1 was showed to have linearity of 0.984 and LoD of 7.9 pM.

The experiment was performed for the methylation levels of 0%, 10%, 25%, 50%, and 100% at the concentrations of 50 pM, 500 pM, 5 nM, 50 nM, and 500 nM of the methylated DNA. The detection limits for the methylation level at each concentration was 50 pM (12.9%), 500 pM (12.6%), 5 nM (9.6%), 50 nM (9.73%), and 500 nM (10.4%).

The concentration and level of methylation of a DNA of an unknown sample may be known through this experiment.

For example, the experiment was performed by preparing 1 nM 10% as an unknown sample. When the sample is concentrated and subjected to the electrochemical sensing to calculate the first current $\Delta$current i, a result of 1.604 $\mu$A was obtained.

When the DNA concentration is calculated by substituting this current value into the first calibration curve of FIG. 13A, a result of 0.83 nM was obtained.

That is, the actual concentration was 1 nM, but the result value corresponding to about 83% was obtained.

After confirming the DNA concentration, the second current ($\Delta$current ii) after MBD1-SiNP binding was calculated to obtain a result of 0.168 $\mu$A.

After the equation corresponding to the five calibration curves of FIG. 13B is obtained, 0.168 $\mu$A was substituted for a y value to calculate a concentration that is an x value. Among them, a value of 1.2 nM that is close to the actual concentration (1 nM) was obtained by substituting $y=0.0335 \ln(x)+0.1612$, which is an equation when the degree of the methylation is 10%.

Finally, the DNA curve (about 0.83 nM) of any sample was confirmed through the calibration curve of FIG. 13A, and as a result, the methylation degree (about 10%) of any sample was confirmed through the calibration curve of FIG. 13B.

Referring to FIG. 14, the experiment was performed on the concentration and level of the methylation of the methylated DNA from the GSTP1 spiked in the human urine sample in the same manner as in FIG. 13.

Accordingly, as illustrated in FIG. 14A, the methylated DNA from the EFEMP1 showed linearity of 0.971 and LoD of 11.8 pM.

At each level of the methylation, the calibration curves for all concentrations and $\Delta$current ii showed more than linearity of 0.93 or more.

The detection limits for the level of the methylation at each concentration were 50 pM (13.4%), 500 pM (12.8%), 5 nM (11.3%), 50 nM (10.2%), and 500 nM (10.3%).

The experiment was performed by preparing 10 nM 25% as an unknown sample. When the sample is concentrated and subjected to the electrochemical sensing to calculate the first current $\Delta$current i, a result of 1.84 $\mu$A was obtained.

When the DNA concentration is calculated by substituting this current value into the second calibration curve of FIG. 14A, a value of 7.2 nM was obtained.

That is, the actual concentration was 10 nM, but the result value corresponding to about 72% was obtained.

After confirming the DNA concentration, the second current ($\Delta$current ii) after the MBD1-SiNP binding was calculated to obtain a result of 0.495 $\mu$A.

After the equation corresponding to the five calibration curves of FIG. 14B is obtained, 0.495 $\mu$A was substituted for a y value to calculate a concentration that is an x value. Among them, a value of 13 nM that is close to the actual concentration (10 nM) was obtained by substituting y=0.0409 ln(x)+0.3891, which is an equation when the degree of the methylation is 25%.

Finally, the DNA curve (about 7.2 nM) of any sample was confirmed through the calibration curve of FIG. 14A, and as a result, the methylation degree (about 25%) of any sample was confirmed through the calibration curve of FIG. 14B.

Hereinafter, a diagnosis device including the diagnosis kit according to an embodiment of the present invention will be described.

The diagnosis device may include a diagnosis kit and a controller. Here, the diagnosis kit may be the diagnosis kit described with reference to FIGS. 1 to 14, but is not limited thereto.

Also, all the contents described with reference to FIGS. 1 to 14 may be applied to the diagnosis device within an acceptable range.

The diagnosis device according to an embodiment of the present invention may include a diagnosis kit and a controller.

The diagnosis kit includes a concentration channel into which a sample containing a methylated DNA is introduced, a concentration chamber connected to the concentration channel and condensed with the methylated DNA by an ion concentration polarization (ICP) phenomenon, a sensing chamber connected to the concentration chamber to allow the methylated DNA inside the concentration chamber to move, allow the methylated DNA moving to the concentration chamber to be hybridized, and allow a methylated DNA binding protein to be bound to the hybridized DNA, and a sensor that acquires a first electrochemical signal inside the sensing chamber when the methylated DNA is hybridized and acquires a second electrochemical signal inside the sensing chamber when the methylated DNA binding protein is bound.

In addition, the diagnosis kit may further include a first valve that allows the concentration chamber and the sensing chamber to communicate with each other or blocks the communication between the concentration chamber and the sensing chamber, a second valve that allows the concentration channel and the concentration chamber to communicate with each other or blocks the communication between the concentration channel and the concentration chamber, and a third valve that presses the inside of the concentration chamber.

In addition, the diagnosis kit may also include a buffer channel, a membrane, and a fourth valve.

The controller may control an overall operation of the diagnosis device.

Specifically, the controller may control the sensor to acquire the first electrochemical signal and the second electrochemical signal.

In addition, the controller may control operations of the plurality of valves. For this, the diagnosis device may further include a valve driver.

Specifically, the controller controls the second valve to allow the concentration channel and the concentration chamber to communicate with each other while the methylated DNA is concentrated and controls the second valve to block the communication between the concentration channel and the concentration chamber when the methylated DNA moves into the concentration chamber.

The controller may control the first valve to allow the concentration chamber and the sensing chamber to communicate with each other after the communication between the concentration channel and the concentration chamber is blocked.

The controller may control the third valve to press the inside of the concentration chamber when the first valve allows the concentration chamber and the sensing chamber to communicate with each other.

The controller may also control the fourth valve to open the fourth valve while the third valve presses the concentration chamber. In addition, the controller may close the sensing chamber by closing the first valve and the fourth valve together.

The controller may apply a first voltage and a second voltage to a sensing electrode.

In addition, the controller may apply a potential to a right portion Vapp of the concentration channel and a left portion GND of the buffer channel.

In addition, the controller may inject a sample containing the methylated DNA into the concentration channel or inject the methylated DNA binding protein into the sensing chamber. For this, the diagnosis device may further include a sample injection part.

The controller may calculate a concentration of methylated DNA based on the first electrochemical signal.

Specifically, the sensor may acquire the first electrochemical signal. Here, the first electrochemical signal may be a current value measured as a voltage is applied to the sensing electrode.

In this case, the controller may calculate first current Δcurrent i using a current value corresponding to the first electrochemical signal. In more detail, the controller may calculate first current Δcurrent i using a current value and a blank current value corresponding to the first electrochemical signal.

The diagnosis device may include a storage part, in which a first calibration equation for the target gene is stored.

Here, the first calibration equation may be derived by experiments and may be represented by the following equation.

$$y = a \cdot \ln(x) + b$$

Here, y may mean the first current Δcurrent i, and x may mean a concentration of methylated DNA. In addition, a and b may be constants.

The constants a and b of the first calibration equation may vary depending on the target gene.

For example, when the target gene is a first gene (GSTP1), a may be 0.2085, and b may be 1.6427. When the target gene is a second gene (EFEMP1), a may be 0.238 and b may be 1.3702.

The controller may calculate a concentration (x) of the methylated DNA by using the calculated first current Δcurrent i (y) and the first calibration equation.

The controller may also display the calculated concentration.

In the foregoing embodiment, the calibration equation is stored in the storage part, but the present invention is not limited thereto. In the storage part, the DNA concentrations according to the first current value Δcurrent i for each target gene may be stored in a table. In this case, the controller may calculate the concentration of the methylated DNA by using the calculated first current value Δcurrent i and the concentration table.

The controller may calculate the methylation degree of the methylated DNA based on the second electrochemical signal.

Specifically, the sensor may acquire the second electrochemical signal. Here, the first electrochemical signal may be a current value measured as a voltage is applied to the sensing electrode.

In this case, the controller may calculate second current Δcurrent ii using a current value corresponding to the second electrochemical signal. In more detail, the controller may calculate second current Δcurrent ii using a current value corresponding to the first electrochemical signal and a current value corresponding to the second electrochemical signal.

The storage part may store a second calibration equation for the target gene.

Here, the second calibration equation may be derived by experiments and may be represented by the following equation.

$$y = c \cdot \ln(x) + d$$

Here, y may mean the second current Δcurrent ii, and x may mean a concentration of methylated DNA. In addition, c and d may be constants.

The second calibration equation may be provided in plurality. For example, the second calibration equation may include a second-1 calibration equation corresponding to a degree of methylation of 0%, a second-2 calibration equation corresponding to a degree of methylation of 10%, a second-3 calibration equation corresponding to a degree of methylation of 25%, a second-4 calibration equation corresponding to a degree of methylation of 50% degree, and a second-5 calibration equation corresponding to a degree of methylation of 100%.

Constants of the above calibration equations may vary depending on the target gene and the corresponding degree of methylation.

The controller may calculate the methylation degree of the methylated DNA by using the calculated second Δcurrent ii (y), the concentration of the methylated DNA (x), and the plurality of second calibration equations.

For example, if an error is the smallest when the second current Δcurrent ii (y) and the concentration of the methylated DNA (x) are substituted into the second-3 calibration equation, the controller may determine that the degree of the methylation of the methylated DNA is 25%, which is the methylation degree corresponding to the second-3 calibration equation.

In this case, the controller may display the determined degree of the methylation.

In the above embodiment, the calibration equation may be stored in the storage part, but the present invention is not limited thereto, and the storage part may be configured to store the concentration of the DNA corresponding to each of the plurality of second currents Δcurrent ii and the plurality of second currents Δcurrent ii for each degree of the methylation in a table. In this case, the controller may calculate the methylation degree of the methylated DNA based on the calculated second current Δcurrent ii, the calculated DNA concentration, and the table.

According to the present invention, since the concentration chamber and the sensing chamber are provided in one kit, and the valve is disposed in the one kit, the concentration, the movement, the incubation, the electrochemical sensing may be all possible in the one kit, and thus, there may be advantages to detect the concentration of the DNA and the level of the methylation at a time.

In addition, the diagnosis kit according to the present invention may use the microfluidic chip to detect the level of the DNA methylation with the small amount of sample (10 μL).

In addition, the methylated DNA that is the target may be detected with the relatively short time (within 2 hours after putting the sample) in the label-free manner without the separate marker.

In addition, the detection limit may be improved through the sample concentration, and since the urine sample of the human is directly used and diagnosed, the convenience may be improved.

In addition, the prostate cancer gene desired to be detected may be spiked to the urine sample of the human and thus detected.

The above-described present invention may be implemented as a computer-readable code on a computer-readable medium in which a program is stored. The computer readable recording medium includes all types which data readable by a computer system is stored. Examples of the computer-readable recording medium include hard disk drives (HDD), solid state disks (SSD), silicon disk drives (SDD), read only memories (ROMs), random access memories (RAMS), compact disc read only memories (CD-ROMs), magnetic tapes, floppy discs, and optical data storage devices. Also, the computer may include a controller.

Thus, the detailed description is intended to be illustrative, but not limiting in all aspects. It is intended that the scope of the present invention should be determined by the rational interpretation of the claims as set forth, and the modifications and variations of the present invention come within the scope of the appended claims and their equivalents.

The invention claimed is:

1. A diagnosis kit comprising:
   a concentration channel into which a sample containing a methylated DNA is introduced;
   a concentration chamber connected to the concentration channel, wherein the methylated DNA is concentrated by an ion concentration polarization (ICP) phenomenon and moves to the concentration chamber;
   a sensing chamber connected to the concentration chamber to allow the methylated DNA inside the concentration chamber to move, allow the methylated DNA moved from inside of the concentration chamber to be hybridized, and allow a methylated DNA binding protein to be bound to the hybridized methylated DNA; and
   a sensor configured to acquire a first electrochemical signal inside the sensing chamber when the methylated DNA is hybridized and acquire a second electrochemical signal inside the sensing chamber when the methylated DNA binding protein is bound.

2. The diagnosis kit according to claim 1, further comprising:
   a first valve configured to allow the concentration chamber and the sensing chamber to communicate with each other or block the communication between the concentration chamber and the sensing chamber; and
   a second valve configured to allow the concentration channel and the concentration chamber to communicate with each other or block the communication between the concentration channel and the concentration chamber,
   wherein the second valve is configured to allow the concentration channel and the concentration chamber to communicate with each other while the methylated DNA is concentrated and block the communication between the concentration channel and the concentration chamber when the methylated DNA moves into the concentration chamber, and the second valve is configured to allow the concentration chamber and the sensing chamber to communicate with each other after blocking the communication between the concentration channel and the concentration chamber.

3. The diagnosis kit according to claim 2, further comprising a third valve configured to press the inside of the concentration chamber when the first valve allows the concentration chamber and the sensing chamber to communicate with each other.

4. The diagnosis kit according to claim 3, wherein the first valve is configured to block the communication between the concentration chamber and the sensing chamber when the concentration chamber and the sensing chamber communicate with each other so that the methylated DNA within the concentration chamber moves to the sensing chamber.

5. The diagnosis kit according to claim 4, further comprising a fourth valve configured to block the communication between the sensing chamber and the outside in addition to the blocking of the communication between the concentration chamber and the sensing chamber through the first valve.

6. The diagnosis kit according to claim 1, wherein the first electrochemical signal is a current value used to calculate a concentration of the methylated DNA, and the second electrochemical signal is a current value used to calculate a level of methylation of the methylated DNA in addition to the concentration of the methylated DNA.

7. The diagnosis kit according to claim 1, wherein the diagnosis kit is a diagnosis kit for diagnosing prostate cancer, and the hybridization is a process of binding ssDNA having a sequence complementary to GSTP1 or EFEMP1 to the methylated DNA.

8. A diagnosis method comprising:
concentrating a methylated DNA by an ion concentration polarization (ICP) phenomenon to move to a concentration chamber;
allowing the methylated DNA within the concentration chamber to move to a sensing chamber;
acquiring a first electrochemical signal within the sensing chamber when the methylated DNA moving to the sensing chamber is hybridized;
binding a methylated DNA binding protein to the hybridized DNA; and
acquiring a second electrochemical signal within the sensing chamber when the methylated DNA binding protein is bound.

9. The diagnosis method according to claim 8, further comprising:
allowing a concentration chamber channel and the concentration chamber to communicate with each other while the methylated DNA is concentrated;
blocking the communication between the concentration chamber channel and the concentration chamber when the methylated DNA moves to the concentration chamber; and
allowing the concentration chamber and the sensing chamber to communicate with each other after blocking the communication between the concentration chamber channel and the concentration chamber.

10. The diagnosis method according to claim 9, wherein the moving of the methylated DNA within the concentration chamber to the sensing chamber comprises pressing the inside of the concentration chamber when the concentration chamber and the sensing chamber communicate with each other.

11. The diagnosis method according to claim 10, further comprising blocking the communication between the concentration chamber and the sensing chamber when the concentration chamber and the sensing chamber communicate with each other so that the methylated DNA within the concentration chamber moves to the sensing chamber.

12. The diagnosis method according to claim 11, wherein the blocking of the communication between the concentration chamber and the sensing chamber comprises blocking communication between the sensing chamber and the outside in addition to the blocking of the communication between the concentration chamber and the sensing chamber through a first valve.

13. The diagnosis method according to claim 8, wherein the first electrochemical signal is a current value used to calculate a concentration of the methylated DNA, and the second electrochemical signal is a current value used to calculate a level of methylation of the methylated DNA in addition to the concentration of the methylated DNA.

14. The diagnosis method according to claim 8, wherein the diagnosis method is performed by a diagnosis kit for diagnosing prostate cancer, and the hybridization is a process of binding ssDNA having a sequence complementary to GSTP1 or EFEMP1 to the methylated DNA.

* * * * *